(12) United States Patent
Antonia

(10) Patent No.: US 11,071,775 B2
(45) Date of Patent: Jul. 27, 2021

(54) COMBINATION IMMUNOTHERAPY FOR TREATING CANCER

(71) Applicant: H. Lee Moffitt Cancer Center and Research Institute, Inc., Tampa, FL (US)

(72) Inventor: Scott Antonia, Land O'Lakes, FL (US)

(73) Assignee: H. LEE MOFFITT CANCER CENTER AND RESEARCH INSTITUTE, INC., Tampa, FL (US)

( * ) Notice: Subject to any disclaimer, the term of this patent is extended or adjusted under 35 U.S.C. 154(b) by 99 days.

(21) Appl. No.: 15/563,847

(22) PCT Filed: Apr. 4, 2016

(86) PCT No.: PCT/US2016/025912
§ 371 (c)(1),
(2) Date: Oct. 2, 2017

(87) PCT Pub. No.: WO2016/161441
PCT Pub. Date: Oct. 6, 2016

(65) Prior Publication Data
US 2018/0078628 A1 Mar. 22, 2018

Related U.S. Application Data

(60) Provisional application No. 62/142,917, filed on Apr. 3, 2015.

(51) Int. Cl.
| | |
|---|---|
| *A61K 35/15* | (2015.01) |
| *C12N 7/00* | (2006.01) |
| *A61K 35/761* | (2015.01) |
| *A61K 39/00* | (2006.01) |
| *C07K 14/47* | (2006.01) |
| *A61K 48/00* | (2006.01) |
| *A61K 45/06* | (2006.01) |
| *C12N 15/86* | (2006.01) |
| *A61K 31/203* | (2006.01) |
| *A61K 39/395* | (2006.01) |
| *C07K 16/28* | (2006.01) |

(52) U.S. Cl.
CPC .... *A61K 39/001151* (2018.08); *A61K 31/203* (2013.01); *A61K 35/761* (2013.01); *A61K 39/0011* (2013.01); *A61K 39/3955* (2013.01); *A61K 45/06* (2013.01); *A61K 48/00* (2013.01); *A61K 48/0066* (2013.01); *C07K 14/4746* (2013.01); *C07K 16/2827* (2013.01); *C12N 7/00* (2013.01); *C12N 15/86* (2013.01); *A61K 35/15* (2013.01); *A61K 2039/5154* (2013.01); *A61K 2039/5156* (2013.01); *A61K 2039/5256* (2013.01); *A61K 2039/545* (2013.01); *A61K 2039/585* (2013.01); *C07K 2317/24* (2013.01); *C07K 2317/76* (2013.01); *C12N 2710/10043* (2013.01)

(58) Field of Classification Search
CPC .. A61K 35/15; A61K 39/0011; C12N 5/0639; C12N 7/00
USPC ...................................... 424/133.1
See application file for complete search history.

(56) References Cited

U.S. PATENT DOCUMENTS

| | | | |
|---|---|---|---|
| 5,643,786 | A | 7/1997 | Cohen et al. |
| 5,788,963 | A | 8/1998 | Murphy et al. |
| 8,008,449 | B2 | 8/2011 | Korman et al. |
| 8,552,154 | B2 | 10/2013 | Freeman et al. |
| 8,617,546 | B2 | 12/2013 | Kang et al. |
| 8,668,905 | B2 | 3/2014 | Antonia et al. |
| 2007/0003550 | A1 | 1/2007 | Antonia et al. |
| 2012/0003179 | A1 | 1/2012 | Readett et al. |
| 2013/0142805 | A1 | 6/2013 | Jure-Kunkel et al. |
| 2015/0044240 | A1 | 2/2015 | Antonia et al. |

OTHER PUBLICATIONS

Espenschied et al. (J Immunol 2003; 170: 3401-3407).*
Mirza et al. (Cancer Res 2006, 66(18): 9299-307).*
Antonia et al., "Combination of p53 cancer vaccine with chemotherapy in patients with extensive stage small cell lung cancer," *Clin. Cancer Res.*, 12(3 Pt 1):878-87, 2006.
Becker et al., "Chapter 8: Use of Recombinant Adenovirus for Metabolic Engineering of Mammalian Cells," *Meth. Cell Biol.*, 43:161-189, 1994.
Brahmer et al., "Safety and activity of anti-PD-L1 antibody in patients with advanced cancer," *N. Engl. J. Med.*, 366(26):2455-65, 2012.
Brossart et al., "Virus-mediated delivery of antigenic epitopes into dendritic cells as a means to induce CTL," *J. Immunol.* 158(7):3270-6, 1997.
Chiappori et al., "INGN-225: a dendritic cell-based p53 vaccine (Ad.p53-DC) in small cell lung cancer: observed association between immune response and enhanced chemotherapy effect," *Expert Opin. Biol. Ther.*, 10(6):983-91, 2010.
Dietz et al., "High efficiency adenovirus-mediated gene transfer to human dendritic cells," *Blood*, 91(1):392-8, 1998.
Extended European Search Report issued in European Patent Application No. 16774419.2, dated Oct. 25, 2018.
Gabrilovich et al., "Coordinated regulation of myeloid cells by tumours," *Nat. Rev. Immunol.*, 12:253-68, 2012.
Ishida et al., "Dendritic cells transduced with wild-type p53 gene elicit potent anti-tumour immune responses," *Clin. Exp. Immunol.*, 117:244-51, 1999.
Kong et al., "Opportunistic Autoimmune Disorders Potentiated by Immune-Checkpoint Inhibitors Anti-CTLA-4 and Anti-PD-1," *Front Immunol.*, 5:206, pp. 1-8, 2014.
Massarelli et al., "Immunotherapy in lung cancer," *Translational Lung Cancer Research*, 3(1):53-63, 2014.

(Continued)

*Primary Examiner* — Yan Xiao
(74) *Attorney, Agent, or Firm* — Parker Highlander PLLC

(57) ABSTRACT

A method is disclosed for treating small cell lung cancer (SCLC) in a subject that involves administering to the subject a therapeutically effective amount of dendritic cells engineered to overexpress p53. In some embodiments, the method further involves administering to the subject a therapeutically effective amount of all-trans-retinoic acid (ATRA). The method can also involve administering to the subject a therapeutically effective amount of an immune checkpoint inhibitor.

22 Claims, 6 Drawing Sheets

(56) References Cited

OTHER PUBLICATIONS

Nikitina et al. "An effective immunization and cancer treatment with activated dendritic cells transduced with full-length wild-type p53," *Gene Ther.*, 9(5):345-52, 2002.
Office Communication issued in Canadian Patent Application No. 2,985,055, dated Nov. 14, 2018.
PCT International Search Report and Written Opinion issued in International Application No. PCT/US2016/025912, dated Apr. 6, 2016.
Topalian et al., "Safety, activity, and immune correlates of anti-PD-1 antibody in cancer," *The New England Journal of Medicine*, 366(26):2443-2454, 2012.
Villacruz et al., "Immunotherapy in lung cancer," *Translational Lung Cancer Research*, 3(1):2-14, 2014.
Wan et al., "Dendritic cells transduced with an adenoviral vector encoding a model tumor-associated antigen for tumor vaccination," *Human Gene Therapy*, 8(11):1355-63, 1997.
Buchbinder and Desai, "CTLA-4 and PD-1 Pathways. Similarities, Differences, and Implications of Their Inhibition," *Am. J. Gin. Oncol.*, 39:98-106, 2016.

\* cited by examiner

COMBINATION IMMUNOTHERAPY FOR TREATING CANCER

CROSS-REFERENCE TO RELATED APPLICATIONS

This application is a national stage application filed under 35 U.S.C.§ 371 of PCT Application No. PCT/US2016/025912, filed Apr. 4, 2016, which claims the benefit of U.S. Provisional Application No. 62/142,917, filed Apr. 3, 2015, which is hereby incorporated herein by reference in its entirety.

BACKGROUND

In the United States, 215,000 new cases of lung cancer were diagnosed and 161,840 patients with lung cancer died in 2008 (Jemal A, et al. CA Cancer J Clin 2008 58:71-96), with small cell lung cancer (SCLC) accounting for 13-15% of them. SCLC typically disseminates early, with 70-80% of patients diagnosed with metastatic disease (extensive stage, ES-SCLC), and is initially also chemo-responsive, so that considerable survival improvements are achieved with (first-line) chemotherapy (Johnson D H. Chest 1999 116: 525S-30S; Johnson B E. Clin Chest Med 2002 23:225-39; Simon G R, et al. Chest 2003 123:259S-71S).

Etoposide-platinum remains the preferred first-line treatment and the standard against which new therapies are measured. By this standard, patients with ES-SCLC achieve overall response rates (ORR) of ≥70% and complete response rates of 20-30%, but rarely survive beyond 2 years (10-20%), with median survival times (MST) ranging from 7 to 10 months (Johnson D H. Chest 1999 116:525S-30S; Johnson B E. Clin Chest Med 2002 23:225-39; Simon G R, et al. Chest 2003 123:259S-71S). The ORR to second-line therapy is also very disappointing and dependent on the previous chemotherapy response. Patients with "platinum-sensitive" disease (ORR=20-25%) progress≥90 days after initial chemotherapy, whereas those with "platinum-resistant" (ORR≤10%) disease progress before (von Pawel J, et al. J Clin Oncol 1999 17:658-67; Ardizzoni A. Oncologist 2004 9 Suppl 6:4-13; Davies A M, et al. Hematol Oncol Clin North Am 2004 18:387-416). New therapies are urgently needed.

SUMMARY

A method is disclosed for treating cancers, such as small cell lung cancer (SCLC), in a subject that involves administering to the subject a therapeutically effective amount of dendritic cells engineered to overexpress p53 in combination with an effective amount of all-trans-retinoic acid (ATRA), and effective amount of an immune checkpoint inhibitor, or a combination thereof. For example, the immune checkpoint inhibitor can be an anti-PD-1 antibody, an anti-PD-L1 antibody, an anti-CTLA-4 antibody, or any combination thereof.

In some embodiments, the dendritic cells comprise an adenovirus vector containing a nucleic acid encoding p53 operably linked to an expression control sequence.

In some embodiments, the method comprises administering at least 1, 2, 3, 4, or 5 doses of dendritic cells at $1 \times 10^6$ to $1 \times 10^7$ cells per dose, including about $1 \times 10^6$, $2 \times 10^6$, $3 \times 10^6$, $4 \times 10^6$, $5 \times 10^6$, $6 \times 10^6$, $7 \times 10^6$, $8 \times 10^6$, $9 \times 10^6$, and $1 \times 10^7$ cells per dose. These doses can be administered at 1, 2, 3, 4, 5, 6 day intervals or 1, 2, 3, or 4 week intervals.

In some embodiments, the ATRA is administered to the subject at least 1, 2, 3, 4, 5, 6, or 7 days prior to administration of the dendritic cells. The ATRA can be administered to the subject in a single dose or in multiple doses. In some embodiments, the ATRA is administered daily prior to administration of the dendritic cells.

The ATRA and immune checkpoint inhibitors can be combined with the engineered dendritic cells in the same composition, administered separately, or any combination thereof. Therefore, also disclosed is a composition comprising engineered dendritic cells and at least one of an ATRA and an immune checkpoint inhibitor.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
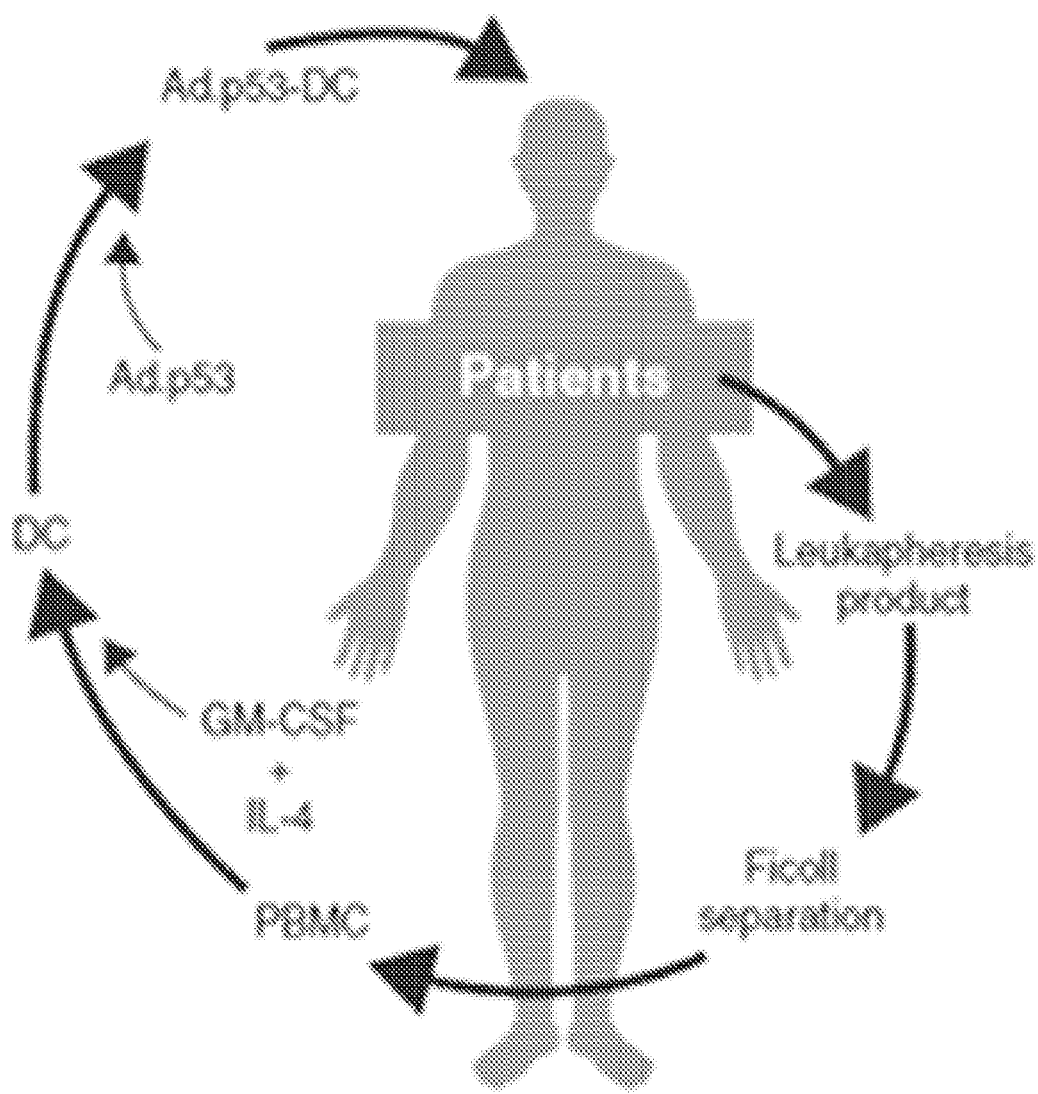
FIG. 1 illustrates a method for obtaining, processing, and administering engineered DCs.

Dendritic cells (DCs) represent unique antigen-producing cells capable of sensitizing T cells to both new and recall antigens. In fact, these cells are the most potent antigen-producing cells. The goal of DC based cancer immunotherapy is to use the cells to prime specific antitumor immunity through the generation of effector cells that attack and lyse tumors.

In some embodiments, the DCs are generated by in vitro differentiation from haematopoietic stem cells or peripheral blood monocytes. For example, a method of culturing and inducing the differentiation of monocytes into dendritic cells has been described in U.S. Pat. No. 5,849,589, which is incorporated herein by reference for these teachings. In particular, this can involve a culture medium stimulated with GM-CSF, IL-4 and TNFα. An alternate method of isolating dendritic cells has been described in U.S. Pat. No. 5,643,786, which is incorporated herein by reference for these teachings. This method involves elutriating peripheral blood samples in at least four flow rates from an elutriation rotor. Calcium ionophore can be used to stimulate monocytes isolated during the process into dendritic cells. Methods and compositions for use of human dendritic cells to activate T-cells for immunotherapeutic responses against primary and metastatic prostate cancer have also been described in U.S. Pat. No. 5,788,963, which is incorporated herein by reference for these methods.

The disclosed DCs are genetically engineered to express p53. In some embodiments, the DCs are genetically engineered according to methods described in U.S. Pat. No. 8,668,905, which is incorporated by reference for the teaching of these DC constructs.

Expression of p53 may be achieved by recombinant DNA technology using techniques well known in the art. Such methods can be used to construct expression vectors containing a chosen nucleotide sequence and appropriate transcriptional and translational control signals. These methods include, for example, in vitro recombinant DNA techniques, synthetic techniques, and in vivo genetic recombination. (See generally, Sambrook et al. (1989) Molecular Cloning Vols. I-III, Cold Spring Harbor Laboratory Press, Cold Spring Harbor, N.Y., and Ausubel et al., Current Protocols in Molecular Biology (1989) John Wiley & Sons, all Vols. and periodic updates thereof, herein incorporated by reference). Alternatively, RNA capable of encoding chosen nucleotide sequences may be chemically synthesized using, for example, synthesizers. See, for example, the techniques described in "Oligonucleotide Synthesis", 1984, Gait, M. J. ed., IRL Press, Oxford, which is incorporated by reference herein in its entirety.

Methods of achieving the expression of p53 (or other gene products) in cultured cells include, but are not limited to, integrating a polynucleotide encoding the gene product into the chromosome of the cell or transforming the cell to carry the gene extrachromasomally.

Generally, an expression vector will comprise a promoter operably linked to nucleotide sequences encoding the desired gene product and containing a transcriptional initiation sequence, and a transcriptional terminator. The promoter should be one that is transcriptionally active in the cell, and may be inducible or constitutive. The gene product encoded by the expression vector may be one that naturally occurs in the cell, or may be from a different cell type or species.

The expression construct should also encode appropriate recognition sequences for translational initiation in the cell. Optionally, the expression construct may contain signals for intracellular targeting of the gene product. For example, nuclear localization of a translational gene product may be increased by methods that are known to those of skill in the art. Finally, the vector may be designed for extrachromosomal maintenance, or for recombination into the chromosome.

Appropriate promoter sequences, transcriptional and translational initiation sequences, and terminators for a given host cell are well known. Expression vectors for various hosts are well known to those of ordinary skill in the art. Promoters used in biotechnology are of different types according to the intended type of control of gene expression. They can be generally divided into constitutive promoters, tissue-specific or development-stage-specific promoters, inducible promoters, and synthetic promoters.

In some embodiments, the disclosed p53-expressing DCs are administered to a subject in combination with all-trans retinoic acid (ATRA). ATRA is one of the active metabolites of Vitamin A (VA). ATRA and associated retinoids are lipophilic molecules that can pass through plasma membranes and enter the nucleus where they bind retinoic acid receptors (RARs). These receptors are members of the nuclear receptor family and can be divided into 2 subgroups, Retinoid Acid Receptor (RAR) and Retinoid X Receptor (RXR). ATRA can bind both but has higher affinity to RAR. Ligation of ATRA to its receptors induces allosteric changes that allow RARs to bind specific DNA recognition sites and regulate gene transcription. The term "ATRA" as used herein refers to all trans retinoic acid or salts of all trans retinoic acid, C1-C10 alkyl esters of all trans retinoic acid, salts of C1-C10 alkyl esters of all trans retinoic acid, C1-C10 alkyl amides of all trans retinoic acid, or salts of C1-C10 alkyl amides of all trans retinoic acid. ATRA is, amongst others, available as Atragen®, Avita®, Renova®, Retin-A®, Vesanoid®, Vitinoin®, Lipo ATRA, Tretinoin Liposomal, AR-623, or Tretinoin®.

In some embodiments, the disclosed p53-expressing DCs are administered to a subject in combination with a checkpoint inhibitor. The two known inhibitory checkpoint pathways involve signaling through the cytotoxic T-lymphocyte antigen-4 (CTLA-4) and programmed-death 1 (PD-1) receptors. These proteins are members of the CD28-B7 family of co-signaling molecules that play important roles throughout all stages of T cell function. The PD-1 receptor (also known as CD279) is expressed on the surface of activated T cells. Its ligands, PD-L1 (B7-H1; CD274) and PD-L2 (B7-DC; CD273), are expressed on the surface of APCs such as dendritic cells or macrophages. PD-L1 is the predominant ligand, while PD-L2 has a much more restricted expression pattern. When the ligands bind to PD-1, an inhibitory signal is transmitted into the T cell, which reduces cytokine production and suppresses T-cell proliferation. A list of immune-checkpoint targeting antibodies in clinical trials is provided in Table 1.

TABLE 1

Clinically evaluated immune-checkpoint blocking antibodies

| Target | Antibody |
| --- | --- |
| CTLA-4 | Ipilimumab |
|  | (MDX-010) |
|  | Tremelimumab |
|  | (CP-675,206) |
| PD1 | Nivolumab (BMS-936558 or MDX1106) |
|  | CT-011 |
|  | MK-3475 |
| PDL1 | MDX-1105 (BMS-936559) |
|  | MPDL3280A |
|  | MSB0010718C |
| PDL2 | rHIgM12B7 |
| B7-H3 | MGA271 |
| LAG3 | BMS-986016 |

Human monoclonal antibodies to programmed death 1 (PD-1) and methods for treating cancer using anti-PD-1 antibodies alone or in combination with other immunotherapeutics are described in U.S. Pat. No. 8,008,449, which is incorporated by reference for these antibodies. Anti-PD-L1 antibodies and uses therefor are described in U.S. Pat. No. 8,552,154, which is incorporated by reference for these antibodies. Anticancer agent comprising anti-PD-1 antibody or anti-PD-L1 antibody are described in U.S. Pat. No. 8,617,546, which is incorporated by reference for these antibodies.

The disclosed compositions and methods can be used in combination with other cancer immunotherapies. There are two distinct types of immunotherapy: passive immunotherapy uses components of the immune system to direct targeted cytotoxic activity against cancer cells, without necessarily initiating an immune response in the patient, while active immunotherapy actively triggers an endogenous immune response. Passive strategies include the use of the monoclonal antibodies (mAbs) produced by B cells in response to a specific antigen. The development of hybridoma technology in the 1970s and the identification of tumor-specific antigens permitted the pharmaceutical development of mAbs that could specifically target tumor cells for destruction by the immune system. Thus far, mAbs have been the biggest success story for immunotherapy; the top three best-selling anticancer drugs in 2012 were mAbs. Among them is rituximab (Rituxan, Genentech), which binds to the CD20 protein that is highly expressed on the surface of B cell malignancies such as non-Hodgkin's lymphoma (NHL). Rituximab is approved by the FDA for the treatment of NHL and chronic lymphocytic leukemia (CLL) in combination with chemotherapy. Another important mAb is trastuzumab (Herceptin; Genentech), which revolutionized the treatment of HER2 (human epidermal growth factor receptor 2)-positive breast cancer by targeting the expression of HER2.

In order to actively drive an antitumor immune response, therapeutic cancer vaccines have been developed. Unlike the prophylactic vaccines that are used preventatively to treat infectious diseases, therapeutic vaccines are designed to treat established cancer by stimulating an immune response against a specific tumor-associated antigen. In 2010, sipuleucel-T (Provenge; Dendreon Corporation) was approved by the FDA for the treatment of metastatic, castration-resistant prostate cancer based on the results of the IMPACT (Immunotherapy Prostate Adenocarcinoma Treatment) trial in which it improved OS by 4.1 months and reduced the risk of death by 22% versus placebo. The advantage of active immunotherapies is that they have the potential to provide long-lasting anticancer activity by engaging both the innate and adaptive arms of the immune response. While mAbs are typically considered passive immunotherapies, there is increasing evidence that they also induce an adaptive immune response via a "vaccination-like" effect.

Generating optimal "killer" CD8 T cell responses also requires T cell receptor activation plus co-stimulation, which can be provided through ligation of tumor necrosis factor receptor family members, including OX40 (CD134) and 4-1BB (CD137). OX40 is of particular interest as treatment with an activating (agonist) anti-OX40 mAb augments T cell differentiation and cytolytic function leading to enhanced anti-tumor immunity against a variety of tumors.

Numerous anti-cancer drugs are available for combination with the present method and compositions. The following is a non-exhaustive lists of anti-cancer (anti-neoplastic) drugs that can be used in conjunction with irradiation: Acivicin; Aclarubicin; Acodazole Hydrochloride; AcrQnine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil I 131; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Gold Au 198; Hydroxyurea; Idarubicin Hydrochloride; Ifosfamide; Ilmofosine; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safmgol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride.

The cancer of the disclosed methods can be any cell in a subject undergoing unregulated growth, invasion, or metastasis. In some aspects, the cancer can be any neoplasm or tumor for which radiotherapy is currently used. Alternatively, the cancer can be a neoplasm or tumor that is not sufficiently sensitive to radiotherapy using standard methods. Thus, the cancer can be a sarcoma, lymphoma, leukemia, carcinoma, blastoma, or germ cell tumor. A representative but non-limiting list of cancers that the disclosed compositions can be used to treat include lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, and pancreatic cancer. In some embodiments, the cancer is small cell lung cancer (SCLC).

Also disclosed is a composition, e.g., a pharmaceutical composition, containing an engineered dendritic cells and an ATRA, an immune checkpoint inhibitor, or a combination thereof, formulated together with a pharmaceutically acceptable carrier. Pharmaceutical compositions can be administered in combination therapy, i.e., combined with other agents.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, immunoconjugate, or bispecific molecule, may be coated in a material to protect the compound from the action of acids and other natural conditions that may inactivate the compound.

The disclosed pharmaceutical composition may include one or more pharmaceutically acceptable salts. A "pharmaceutically acceptable salt" refers to a salt that retains the desired biological activity of the parent compound and does not impart any undesired toxicological effects.

The disclosed pharmaceutical composition may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

Actual dosage levels of the active ingredients in the pharmaceutical compositions may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" preferably results in a decrease in severity of disease symptoms, an increase in frequency and duration of disease symptom-free periods, or a prevention of impairment or disability due to the disease affliction. For example, for the treatment of tumors, a "therapeutically effective dosage" preferably inhibits cell growth or tumor growth by at least about 20%, more preferably by at least about 40%, even more preferably by at least about 60%, and still more preferably by at least about 80% relative to untreated subjects. The ability of a compound to inhibit tumor growth can be evaluated in an animal model system predictive of efficacy in human tumors. Alternatively, this property of a composition can be evaluated by examining the ability of the compound to inhibit, such inhibition in vitro by assays known to the skilled practitioner. A therapeutically effective amount of a therapeutic compound can decrease tumor size, or otherwise ameliorate symptoms in a subject. One of ordinary skill in the art would be able to determine such amounts based on such factors as the subject's size, the severity of the subject's symptoms, and the particular composition or route of administration selected.

A composition disclosed herein can be administered via one or more routes of administration using one or more of a variety of methods known in the art. As will be appreciated by the skilled artisan, the route and/or mode of administration will vary depending upon the desired results. Preferred routes of administration for antibodies of the invention include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, the composition can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art.

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The term "therapeutically effective" refers to the amount of the composition used is of sufficient quantity to ameliorate one or more causes or symptoms of a disease or disorder. Such amelioration only requires a reduction or alteration, not necessarily elimination.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "inhibit" refers to a decrease in an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

The term "hyperplastic cell" or "hyperplasm" refers to a cell undergoing physiological (normal) cell proliferation ("hyperplasia").

The term "neoplastic cell" or "neoplasm" refers to a cell undergoing abnormal cell proliferation ("neoplasia"). The growth of neoplastic cells exceeds and is not coordinated with that of the normal tissues around it. The growth typically persists in the same excessive manner even after cessation of the stimuli, and typically causes formation of a tumor. Neoplasms may be benign, premalignant, or malignant.

The term "cancer" or "malignant neoplasm" refers to a cell that displays uncontrolled growth, invasion upon adjacent tissues, and often metastasis to other locations of the body.

The term "tumor" refers to an abnormal mass of tissue containing neoplastic cells.

The term "metastasis" refers to the spread of malignant tumor cells from one organ or part to another non-adjacent organ or part. Cancer cells can "break away," "leak," or "spill" from a primary tumor, enter lymphatic and blood vessels, circulate through the bloodstream, and settle down to grow within normal tissues elsewhere in the body. When tumor cells metastasize, the new tumor is called a secondary or metastatic cancer or tumor.

The term "antibody" refers to natural or synthetic antibodies that selectively bind a target antigen. The term includes polyclonal and monoclonal antibodies. In addition to intact immunoglobulin molecules, also included in the term "antibodies" are fragments or polymers of those immunoglobulin molecules, and human or humanized versions of immunoglobulin molecules that selectively bind the target antigen.

A number of embodiments of the invention have been described. Nevertheless, it will be understood that various modifications may be made without departing from the spirit and scope of the invention. Accordingly, other embodiments are within the scope of the following claims.

EXAMPLES

Example 1

The p53 tumor suppressor gene plays a central role in the control of cell growth and differentiation. Normally, p53 is a short-lived protein localized in the nuclei of cells. Approximately 50% of all human cancers and >90% of patients with SCLC have altered p53 function, mostly as a result of single-point mutations or abnormalities in degradation of wild-type (wt) p53. This leads to accumulation of mutant (mu) or wt-p53 protein (whereas normal tissues have low to undetectable levels) and expression of p53-derived epitopes on the surface of tumor cells in the context of MHC class I (Chikamatsu K, et al. Clin Cancer Res 1999 5:1281-8).

Furthermore, since mutant forms of p53 can result in oncogenic gain of function (Liu D P, et al. Oncogene. 2010 29(7):949-56; van Oijen M G, et al. Clin Cancer Res 2000 6:2138-45) it is unlikely that they can escape anti-p53 cytotoxic T lymphocytes (CTLs) by restoring wt-p53 status (no antigen-loss variants). Thus, p53 has many characteristics of an "ideal" tumor-associated antigen (TAA), which makes it a very attractive candidate target for immune recognition and anti-p53-based cancer immunotherapy.

Different approaches to p53-based cancer immunotherapy have been explored. The role of wt-p53 peptide sequences in the induction of antitumor CTL responses has been investigated in both human and animal in vitro studies, with encouraging results (Chikamatsu K, et al. Clin Cancer Res 1999 5:1281-8; Vierboom M P, et al. J Exp Med 1997 186:695-704; Mayordomo J I, et al. J Exp Med 1996 183:1357-65; Zwaveling S, et al. Cancer research 2002 62:6187-93; Parajuli P, et al. Cancer research 2001 61:8227-34; Eura M, et al. Clin Cancer Res 2000 6:979-86). However, peptide-based approaches assume knowledge of precise HLA types and the peptides present on particular tumors, leading to several limitations (Theobald M, et al. J Exp Med 1998 188:1017-28), such as technical difficulties with generating custom mutant-specific peptides and clinical trial designs that adequately assess this approach.

These difficulties can be circumvented with the use of TAA proteins and dendritic cells (DCs). DCs are the most potent antigen presenting cells (APCs) and the most effective in inducing a primary CTL response. There are numerous methods of loading DCs with a variety of different TAAs, and animal models show that the approach of using viral vectors to introduce these TAAs into DCs is practical, safe, and effective (Brossart P, et al. J Immunol 1997 158:3270-6; Wan Y, et al. Hum Gene Ther 1997 8:1355-63; Specht J M, et al. J Exp Med 1997 186:1213-21). Because cells with mu-p53 usually overexpress the protein and because there is a large human experience in melanoma with targeting overexpressed but not mutant proteins such as MAGE and MART, a much more practical approach would be to develop a strategy that targets the non-mutant portions of the p53 overexpressed in tumors.

Therefore, DCs were transfected with the full-length p53 gene. The rationale for this approach is based on 1) the assumption that multiple MHC class I and II matching p53-derived epitopes are present on the surface of DCs, eliminating the need for selecting matching patients as well as providing conditions for activation of CD4$^+$ T cells, and 2) the fact that previous studies have demonstrated that each of the different minimal epitopes combined in a single fusion protein can be recognized by specific CTLs (Thomson S A, et al. Proc Natl Acad Sci USA 1995 92:5845-9).

Adenovirus (Ad) provides a high-level transduction efficacy for many cell types, regardless of their mitotic status (Becker T C, et al. Meth Cell Biol 1994 43:161-76), and replication-defective Ad (deletions in the E1 region) has been safely injected into patients (Roth J A, et al. J Natl Cancer Inst 1997 89:21-39). Successful transduction of DCs with model antigens has been reported, and transduced DCs have effectively presented the recombinant protein antigens (Brossart P, et al. J Immunol 1997 158:3270-6; Dietz A, et al. Blood 1998 91:392-8; Wan Y, et al. Human Gene Therapy 1997 8:1355-63). In this case, DCs were infected with an adenoviral construct containing wt-p53 to generate Ad.p53-DC.

The process for obtaining, processing, and administering DCs from a subject is illustrated in FIG. 1. DCs were prepared from peripheral blood mononuclear cells (PBMC) collected by leukapheresis, separated over a Ficoll density gradient, washed, suspended in Plasmalyte-A solution, supplemented with autologous plasma and DMSO, and cryostoraged in liquid nitrogen in the Cell Therapy Core at the H. Lee Moffitt Cancer Center.

Preparation of the DC and their characterization was described previously (Antonia S J, et al. Clin Cancer Res 2006 12:878-87; Chiappori A A, et al. Expert Opin Biol Ther 2010 10:983-91). Briefly, after thawing, PBMCs were placed in X-VIVO-15 medium (Biowhittaker, Walkersville, Md.) in tissue culture flasks at a concentration of 1.3-1.7× 10$^6$ cells per cm$^2$. After 2-hr culture non-adherent cells were removed and the flasks were recharged with X-VIVO-15 medium supplemented with 5 ng/ml GM-CSF (Immunex), and 5 ng/ml IL-4 (R&D Systems, Minneapolis, Minn.). The flasks were incubated for 48 hours, at which time additional cytokine supplemented medium was added to the flasks. The flasks were then incubated for an additional 72 hours. The non-adherent and loosely adherent cells were collected and infected with Ad.p53 and incubated for 2 hours after which X-VIVO-15 medium was added for a 10$^6$ cells/ml concentration and cells incubated for an additional 46 hours.

The optimal viral particle to cell ratio used was 15,000:1 as determined for our previous study (Antonia S J, et al. Clin Cancer Res 2006 12:878-87; Chiappori A A, et al. Expert Opin Biol Ther 2010 10:983-91). The vaccine release criteria included: (a) negative Gram's staining; (b) negative *Mycoplasma* test by PCR analysis; (c) maximum endotoxin concentration of 5 EU/mL; and (d) a mature DC-p53 expressing phenotype. DC phenotype was defined as lineage (CD3, CD14, CD19, CD20, CD56) negative, HLA-DR positive, CD86 positive, and p53 positive cells. Intracellular staining for p53 was performed using the kit from Caltag, Burlingame, Calif. DC vaccines in 1 ml were injected intradermally into 4 separate sites (0.25 ml at each site) in bilateral proximal upper and lower extremities (in the regions of the axillary and inguinal nodal basins) three times after the baseline blood samples were drawn and at 2 week intervals.

To determine the optimal dose of Ad.p53 vector that produces the highest level of human p53 expression with the least amount of toxicity to the DCs, mice were given a human p53-transduced DC vaccine (Nikitina E Y, et al. Gene Ther 2002 9:345-52; Ishida T, et al. Clin Exp Immunol 1999 117:244-51). Infecting murine DCs with the Ad.p53 vector at a multiplicity of infection (MOI) of 50-200 viral particles per cell (vp/cell) did not adversely affect DC viability. MOI in excess of 500 significantly reduced DC viability. However, transduction of DCs at an MOI of 100 produced very good transduction efficiency, with 40-45% of the DCs becoming positive for p53. Similarly, infecting human DCs with the Ad.p53 vector at a MOI of 10,000-20,000 vp/cell did not adversely affect DC viability and showed better transduction efficiency with the higher dose. At a MOI of 40,000 vp/cell, DC viability was adversely affected despite transduction rates similar to the lower doses. Thus, 20,000 vp/cell was the MOI chosen to manufacture Ad.p53-DC.

Figure 2:
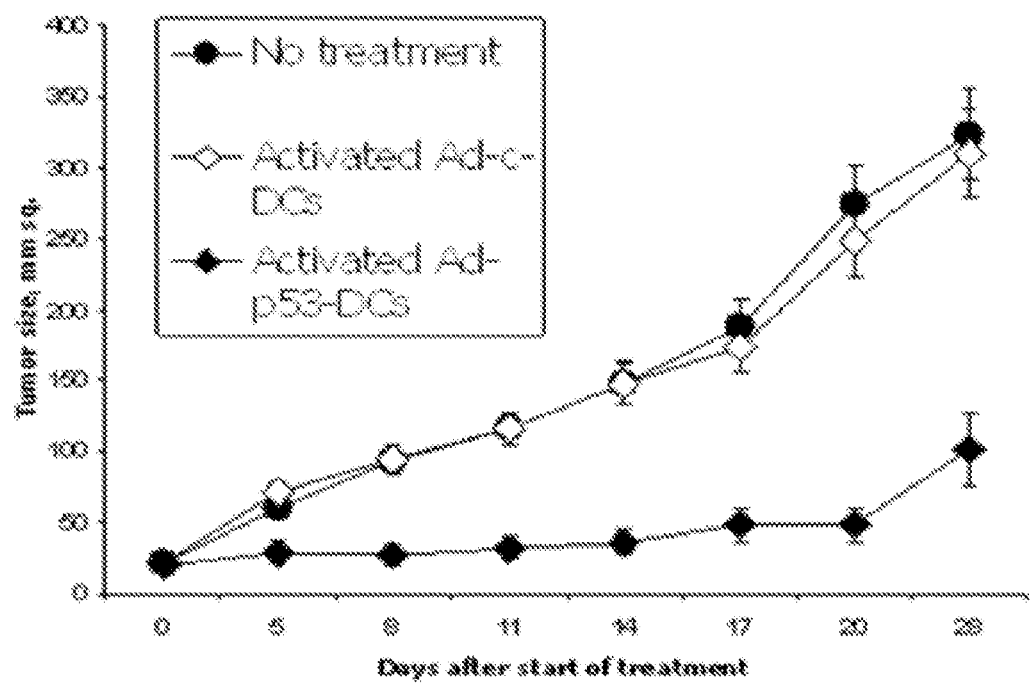
FIG. 2 shows tumor growth for MethA sarcoma-bearing BALB/c mice treated with $6 \times 10^5$ activated Ad.c- or Ad.p53-DCs 4 times on days 0, 5, 11, and 17. Four mice treated with Ad.p53-DCs rejected their tumor.

Additionally, T cells recovered from immunized mice contained significant numbers of CTLs that could specifically kill tumor cells previously modified to express the human p53 gene, and Ad.p53-DC-immunized mice developed a significant CTL response to murine p53, probably due to the significant homology between murine and human p53. Ad.p53-DC-induced anti-p53 CTL response resulted in protection of mice from challenges with tumor cells that overexpressed human or murine p53. Furthermore, tumors that were established in mice prior to immunization exhibited significantly slowed growth as a result of the immunization with Ad.p53-DC (Nikitina E Y, et al. Gene Ther 2002 9:345-52; Ishida T, et al. Clin Exp Immunol 1999 117:244-51) (FIG. 2).

To determine whether this response was sufficient to recognize and eliminate tumor cells in cancer patients, peripheral blood-derived T cells and autologous DCs were obtained from 3 healthy volunteers and 9 cancer patients, all of whom were HLA-A2 positive (Nikitina E Y, et al. Clin Cancer Res 2001 7:127-35). T cells were in vitro primed with Ad.p53-DC and then tested for their ability to kill (HLA-A2-positive) target cells with normal to low or overexpressed levels of p53 protein.

Selective CTL killing of p53-overexpressing cells but not of cells with normal p53 expression levels was generated in blood from all 3 healthy donors and 8 cancer patients. Furthermore, when cells that expressed normal to low levels of p53 were forced to overexpress p53 by gene transfection, they became sensitive to Ad.p53-DC-primed CTLs. Additionally, when an excess of NK cell-sensitive target cells or an anti-CD4 antibody was added to the cytotoxicity assays, very little effect or a small decrease in cytotoxicity activity was seen. Conversely, when anti-CD8 was added, a very significant decrease in cytotoxicity was observed, demonstrating that neither NK nor CD4 cells but CD8-positive CTLs are the relevant effector cells primed with Ad.p53-DC.

Example 2 p53 gene mutations and p53 protein overexpression are present in ≥90% of SCLC cases (D'Amico D, et al. Oncogene 1992 7:339-46; Bodner S M, et al. Oncogene 1992 7:743-9). With many characteristics of an "ideal" TAA present, p53 is an attractive candidate for cancer immunotherapy. Therefore, an approach where an adenoviral vector carrying the intact human wt-p53 gene is used to overexpress the p53 protein in autologous DCs and that allows endogenous processing mechanisms to select and present the appropriate p53 peptides for each individual's HLA type encourages the use of these transduced cells (Ad.p53-DC) as a vaccine.

The trial was designed to assess the clinical and immune response of SCLC to Ad.p53-DC (Chiappori A A, et al. Expert Opin Biol Ther 2010 10:983-91). Fifty-four patients (24 male, 30 female) with extensive stage disease (initial or recurrent) were enrolled. All had previously been treated with chemotherapy. Patients with stable disease or better underwent leukopheresis 8 weeks after the last dose of chemotherapy to manufacture Ad.p53-DC. Patients received 3 doses of Ad.p53-DC intra-dermally every 2 weeks. If after reassessment, stable disease or better persisted, 3 more monthly doses of Ad.p53-DC were given.

The number of p53$^+$ DCs (Ad.p53-DC dose) was evaluated using flow cytometry. The initial goal was to escalate the dose from $5\times10^6$ to $5\times10^7$ p53$^+$ DC. However, generation of >$5\times10^6$ p53$^+$ DC per dose was difficult to achieve (on average, $7.7\times10^7$ DCs and $8.6\times10^6$ p53$^+$ DCs were generated per dose and $\geq10^7$ p53$^+$ DCs were generated in <10% of cases). Thus, to maintain consistency throughout the trial, the single doses of p53$^+$ DC were not escalated beyond $5\times10^6$ cells. On average, each patient received $3.8\times10^6$ p53$^+$ DCs per dose. However, 5 patients received <$10^6$ p53$^+$ DCs because of production difficulties.

Ad.p53-DC toxicities were infrequent and mostly mild. Only 2 patients experienced grade 2 toxicities (1 fatigue, 1 arthralgia), and Ad.p53-DC was never withheld. The most frequent toxicities were grade 1 arthralgia/myalgia (9 patients), fatigue and injection site erythema (5 patients each), and injection site pain (4 patients). Occurrence of toxicities was independent of the number of Ad.p53-DC doses received.

The p53-specific immune response was evaluated by ELISPOT using autologous PBMCs infected with a canary pox virus (ALVAC) containing wt-p53 or empty vector as control. The number of γ-interferon producing cells was evaluated using an automated ELISPOT reader (Chiappori A A, et al. Expert Opin Biol Ther 2010 10:983-91). In 12 HLA-A2-positive patients, immune responses were tested with p53-derived or control HLA-A2 matched peptides pulsed onto autologous PBMCs and tetramers.

Response was considered significant if ≥2 SD higher than the response to ALVAC or peptide controls. Increase over baseline (pre-Ad.p53-DC) was considered significant if p53-specific responses (post-Ad.p53-DC) were ≥2 SD higher than p53-specific responses pre-Ad.p53-DC and at least 2 SD higher than responses to ALVAC or peptides. Because the generation of a p53-specific T-cell response not only depends on the quality of antigen stimulation but also on the functional activity of T cells and DCs in the host, they were also tested (Chiappori A A, et al. Expert Opin Biol Ther 2010 10:983-91).

Full immune response evaluation was possible in 43 patients. Overall, 18 patients (41.8%) had a statistically significant p53-specific response using ALVAC and 7 of 12 patients (58.3%) using p53-derived peptide. Three patients with a significant response to Ad.p53-DC using the p53-derived peptide were not tested with ALVAC (technical reasons). The baseline p53-specific immunity level was similar in Ad.p53-DC responsive and non-responsive patients. The level of the p53-specific immune response decreased 2 months after completing Ad.p53-DC, coinciding with the start of additional chemotherapy.

Presence and functional activity of DCs were both decreased, and the p53-specific immune response to Ad.p53-DC did not correlate with T cell functional activity, presence of Tregs, or pre-existing levels of DC activity. Because myeloid-derived suppressive cells (MDSC) are implicated in the host's immunosuppressive state (Kusmartsev S, et al. Cancer Immunol Immunoth 2002 51:293-8; Gabrilovich D. Nat Rev Immunol 2004 4:941-52), we examined patients for the presence of these cells. Pre-Ad.p53-DC MDSC (Lin$^-$HLA-DR$^-$CD3$^+$) levels were elevated compared to control donors (p=0.01). Post-Ad.p53-DC levels increased even further (p=0.002). All patients with normal levels of MDSCs prior to Ad.p53-DC developed a p53-specific immune response compared to only 33% of patients who had elevated levels of MDSC (p=0.012).

Two patients (3.7%) achieved a partial response (PR), and 13 had stable disease with Ad.p53-DC. All but 5 patients developed progressive disease (PD), and response data were available for 33 patients who received additional chemotherapy post-Ad.p53-DC progression. The ORR for all 33 patients treated with "second"-line chemotherapy was 51.5% and 45.5% for the 22 platinum-resistant patients. The MST (from the date of the first Ad.p53-DC dose) for platinum-resistant patients was 10.5 months (95% CI=5.3-14.4) and 8.8 months (95% CI=5.2-11.8) for all 54 patients.

Figure 3:
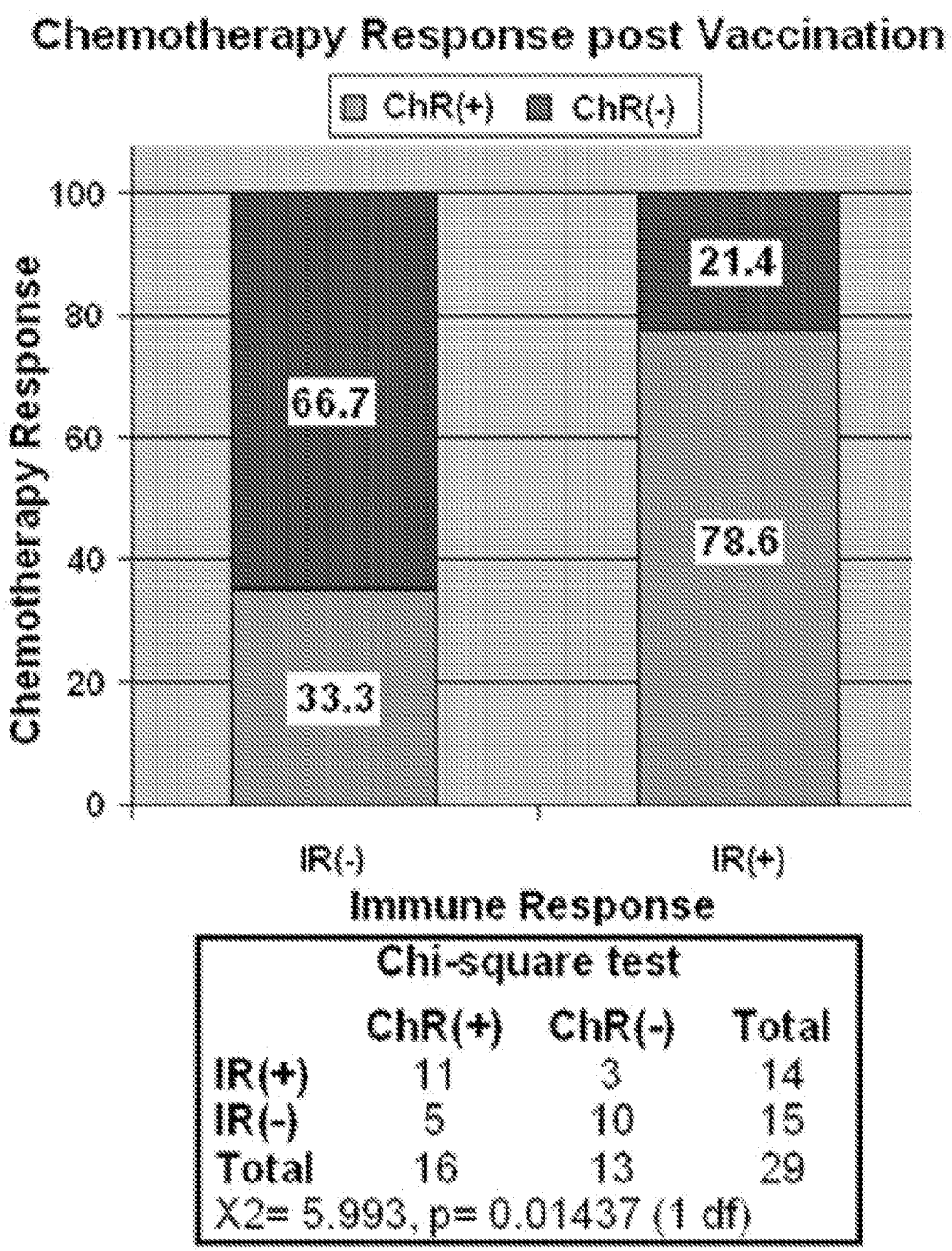
FIG. 3 shows relation between immune response (IR) to Ad.p53-DC and clinical response to second-line chemotherapy (ChR).

The relation between immune response to Ad.p53-DC and clinical response to second-line chemotherapy was also evaluated (FIG. 3). Eleven of 14 patients (78.6%) with a positive immune response experienced a clinical response to second-line chemotherapy compared to 5 of 15 patients (33.3%) with a negative immune response (p=0.014). Patients with a positive immune response had a trend toward improved survival; however, the difference did not reach statistical significance (MST=12.6 vs. 8.2 months, p=0.131) (Chiappori A A, et al. Expert Opin Biol Ther 2010 10:983-91).

Example 3

It is now fully appreciated that tumor-specific immune responses in cancer are inhibited. Large numbers of different factors have been implicated in this process, including regulatory T cells (Treg), myeloid cells, various soluble factors and cytokines, inhibitory molecules expressed by immune and tumor cells, etc. (Rabinovich G A, et al. Annu Rev Immunol 2007 25:267-96; Zou W, et al. Nat Rev Immunol 2008 8:467-77; Munn D H, et al. J Clin Invest 2007 117:1147-54). Among these factors MDSC play a prominent role.

MDSC are a heterogeneous group of pathologically activated immature myeloid cells and myeloid precursors with potent immune suppressive activity (Gabrilovich D I, et al. Nat Rev Immunol 2009 9:162-74; Gabrilovich D I, et al. Nat Rev Immunol 2012 12:253-68; Peranzoni E, et al. Curr Opin Immunol 2010; Ostrand-Rosenberg S, et al. J Immunol 2009 182:4499-506). Two major groups of MDSC have been identified: polymorphonuclear (PMN) and mononuclear (M) MDSC. These cells share common features (immature myeloid cells with immune suppressive activity) but differ in morphology, phenotype, and mechanisms of suppressive activity (Gabrilovich D I, et al. Nat Rev Immunol 2012 12:253-68). In cancer patients, these MDSC have partially overlapping phenotype that can be identified using several markers, which largely depends on the type of tumor. In most tumors, immune suppressive MDSC are defined as Lin$^-$HLA-DR$^-$CD33$^+$ or CD33$^+$CD14$^-$CD11b$^+$ cells that can be further sub-divided into CD15$^+$ PMN-MDSC and CD15$^-$ M-MDSC. In some tumors, most notably melanoma, M-MDSC are defined as CD14$^+$HLA-DR$^{-/lo}$ (Filipazzi P, et al. J Clin Oncol 2007 25:2546-53; Poschke I, et al. Cancer Res 2010 70:4335-45). MDSC are characterized by potent immune suppressive activities in both antigen-specific and non-specific experimental systems.

The association between tumor progression and the presence of MSDC in cancer patients was demonstrated in a number of studies. In patients with solid tumors, a significant correlation between circulating MDSC and clinical cancer stage was observed. Among stage IV patients, those with extensive metastatic tumor burden had the highest percent and absolute number of MDSC (Diaz-Montero C M, et al. Cancer Immunol Immunother 2009 58:49-59). Patients with lower levels of circulating MDSC at baseline and on the last cycle of chemotherapy had significantly higher probability of a pathologic complete response (Montero A J, et al. Breast Cancer Res Treat 2012 132:215-23). Increased circulating MDSC correlated with clinical stage and pathological grade in patients with bladder cancer (Yuan X K, et al. J Int Med Res. 2011 39(4):1381-91; Eruslanov E, et al. Int J Cancer 2011) and pancreatic cancer (Goedegebuure P, et al. Curr Cancer Drug Targets 2011 11:734-51). Recently, first report linked clinical response to vaccination to accumulation of MDSC in patients with renal cell cancer (Walter S, et al. Nat Med. 2012 18(8):1254-61). Experiments in mice demonstrated that elimination of MDSC with antibodies or different compounds could substantially improve antitumor immune responses, which resulted in antitumor effect (Gabrilovich D I, et al. Nat Rev Immunol 2012 12:253-68). However, no data are available testing the hypothesis that depletion of MDSC can improve the effect of cancer vaccines or another immune therapeutic modality in cancer patients.

Because all-trans-retinoic acid (ATRA) causes differentiation of acute promyelocytic leukemia (APL) cells and lineage features between MDSCs and APL cells are comparable, the effect of ATRA on DC differentiation and function was tested in patients with metastatic renal cell carcinoma (Mirza N, et al. Cancer research 2006 66:9299-307). As expected, patients had a substantially increased proportion of MDSCs, decreased presence of DCs, and decreased MDSC/DC ratio. Treatment with ATRA significantly decreased the presence of MDSC and improved MDSC/DC ratio to control levels. Patients had profound defects in the ability to respond to tetanus toxoid and to stimulate allogeneic T cells and treatment with ATRA improved those defects as well, although not significantly.

Gr-1$^+$ cells (analogous to human MDSC) inhibit antigen-specific T cell response and are present in excess in tumor-bearing mice. ATRA differentiates these cells in vitro and removes their immunosuppressive effect (Bronte V, et al. Blood 2000 96:3838-46; Gabrilovich D I, et al. J Immunol 2001 166:5398-406). Furthermore, in vivo administration of ATRA to tumor-bearing mice dramatically reduces the presence of Gr-1$^+$ cells and improves the effect of tumor vaccines (Kusmartsev S, et al. Cancer research 2003 63:4441-9). Similarly, in vitro treatment of human MDSCs with ATRA results in their differentiation (⅔ become DC-like and ⅓ myeloid) (Almand B, et al. J Immunol 2001 166: 678-89). These data confirm the effect of ATRA on DCs and MDSCs and strongly suggest a valuable role in cancer immunotherapy.

It has been shown that: (1) Ad.p53-DC was safe and induced immune responses (IR~40-50%), (2) lack of IR was related to immunosuppressive myeloid derived suppressive cells (MDSCs), (3) a high rate of objective tumor regressions was seen in patients treated with chemotherapy after vaccination, particularly if a positive IR was obtained and (4) ATRA reduces the number of MDSCs and enhances IR. However, confirmation of this evidence required a prospective, comparative (randomized) trial (Alberto A, et al. J Thoracic Oncol (LALCA Supplement) 2014).

Thus, a randomized phase II study was designed and completed to address the question of whether combination of Ad.p53-DC with ATRA improved the clinical outcome of patients. The hypotheses were 1) salvage chemotherapy in combination with Ad.p53-DC results in a substantial improvement in clinical outcomes, and 2) ATRA, by reversing the immunosuppressive influence of MDSCs, substantially improves the p53-specific immune response to Ad.p53-DC and hence clinical outcomes.

Patients with ES-SCLC were enrolled to this randomized phase II study. The trial was registered at ClinicalTrials.gov (NCT00617409). All patients provided a written informed consent and treatment protocol was approved by University of South Florida Institutional Review Board. After receiving initial chemotherapy, (4-6 cycles of a standard platinum/etoposide regimen as first-line chemotherapy), patients were enrolled and randomized. Additional eligibility included; stable disease (SD) or better with Eastern Cooperative Oncology Group (ECOG) performance status of 0 to 1, and adequate organ function were screened for initial registration approximately 4-6 weeks after the completion of first-line chemotherapy. Prophylactic cranial irradiation (PCI) was permitted.

Eligible patients were randomized in a 1:1:1 ratio to one of three treatment arms: Arm A (control patients or observation), Arm B: (patients treated with Ad.p53-DC vaccine only), or Arm C (patients treated with Ad.p53-DC vaccine in combination with ATRA). Each vaccine consisted of 2-5× $10^6$ Ad-p53 DCs. Cells were injected intradermally, at two-week intervals for three times (three vaccine doses). Patients were restaged approximately 2 weeks after the $3^{rd}$ vaccine dose. Patients without signs of disease progression (PD) underwent a second leukapheresis and then vaccinated 3 more times at 4-week intervals. Patients on Arm C also received 150 mg/m² ATRA for 3 days prior to each vaccine administration (followed by vaccine administration on the next day). This scheduling was based on our previous data (Mirza N, et al. Cancer research 2006 66:9299-307) that demonstrate persistence of the ATRA effect on MDSC for minimum 2 weeks.

All patients were followed until evidence of PD at which time they received salvage or second line chemotherapy with single agent paclitaxel (200 mg/m2 IV every 3 weeks, 4-6 cycles).

The primary objective was to evaluate the efficacy of second line paclitaxel in the two experimental regimens (Arms B and C). Objective response (OR) to paclitaxel in each arm was the primary endpoint of the study. An optimal two-stage design was used in planning of this study (Simon R. Control Clin Trials 1989 10:1-10) because it has been successfully applied in randomized phase II trials to rank experimental agents (Wieand H S. J Clin Oncol 2005 23:1794-5). The control arm was used to examine consistency with historical control data and to assure that patients entering the phase II trial are comparable to historical controls. Using the optimal two-stage design, if 3 responses were observed in the first 9 patients, the second stage would accrue 14 additional patients.

Figure 4:
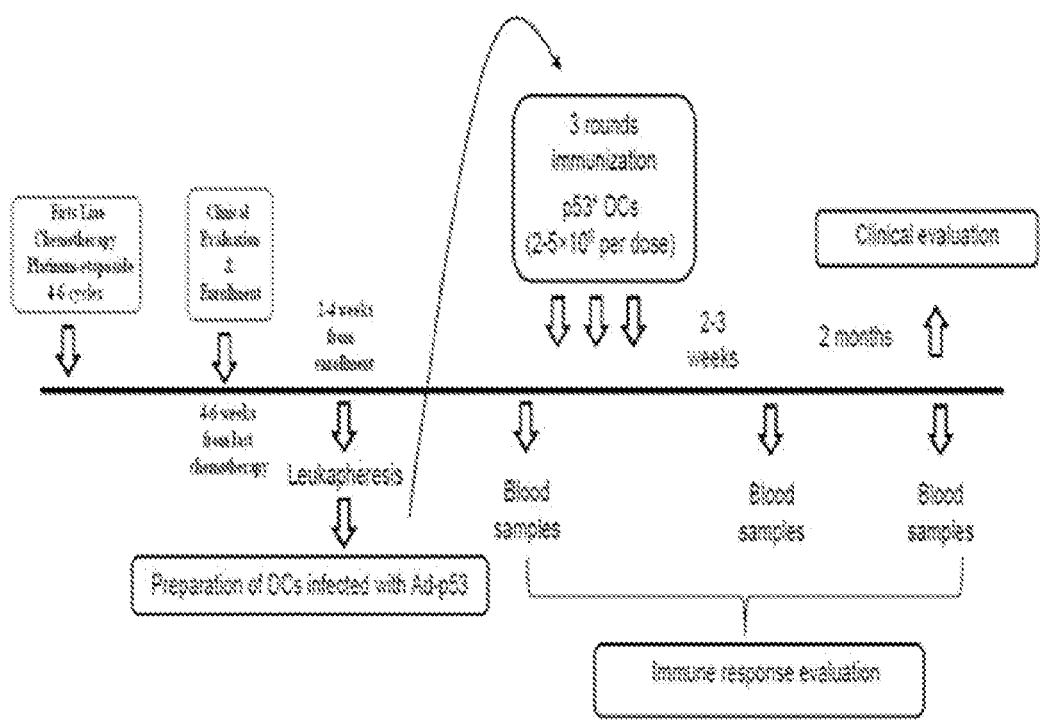
FIG. 4 illustrates a study protocol to evaluate immune response to Ad.p53-DCs.

To assess immune response, PBMCs were collected from patients at different time points during the treatment (FIG. 4) and kept frozen in liquid nitrogen. All samples from one patient were analyzed simultaneously to reduce inter-experimental variability. PBMCs were thawed, incubated overnight in complete medium (RPMI-1640 supplemented with antibiotics and 10% FBS) and then used in experiments. Cell viability was greater than 80%. T-cell responses were assessed using IFN-γ ELISPOT after infection with a recombinant canarypox virus (ALVAC) containing wild-type p53 or empty vector (obtained from Aventis Pasteur, Toronto, Canada), and incubation for 48 hours. Empty ALVAC virus served as a control.

The initial infection step was performed in serum free media (supplemented with cytokines) for 90 minutes after which, complete media was added. In IFN-γ ELISPOT assay $2\times10^5$ PBMCs were seeded in triplicates or quadruplicates in 96-well plates pre-coated with an anti-IFN-γ antibody. To ascertain that T cells are functionally competent for each sample we prepared additional controls (unstimulated or PHA (5 µg/ml) stimulated cells), and the plate was further incubated for 36 hours. The number of IFN-γ producing cells was evaluated as described previously (Antonia S J, et al. Clin Cancer Res 2006 12:878-87) using an automated ELISPOT reader (Cellular Technology, Ltd, OH).

TABLE 2

|  |  | Arm A | Arm B | Arm C | Total |
|---|---|---|---|---|---|
| Subtotal |  | 18 | 19 | 17 | 54 |
| Gender | M | 11 | 7 | 13 | 31 |
|  | F | 7 | 12 | 4 | 23 |
| Age | Median | 63 | 63 | 63 | 62 |
|  | Range | 43-73 | 51-74 | 48-73 | 43-74 |
| Race | White | 16 | 19 | 17 | 52 |
|  | AA/Other | 1/1 | 0/0 | 0 | 1/1 |
| PS | 0 | 4 | 6 | 4 | 14 |
|  | 1 | 14 | 13 | 13 | 40 |
| Chemotherapy | ≤4 cycles | 4 | 5 | 2 | 11 |
|  | >4 cycles | 14 | 14 | 15 | 43 |
| Radiotherapy | PCI | 2 | 3 | 2 | 7 |
|  | WBRT (S) | 3 | 0 | 5 | 8 |
|  | Thoracic | 5 | 3 | 1 | 9 |
|  | Distant | 2 | 1 | 1 | 4 |
| Leukopheresis | Total |  | 24 | 19 | 43 |
|  | 0/1 |  | 1/12 | 0/15 | 1/27 |
|  | 2 |  | 6 | 2 | 8 |
| Vaccinations | Median |  | 3 | 3 | 3 |
|  | Range |  | 0-6 | 1-6 | 0-6 |
|  | <3/3/>3 |  | 4/11/4 | 5/10/2 | 9/21/6 |
|  | Total |  | 56 | 58 | 114 |

54 patients were enrolled during the first stage, 18, 19 and 17 in arms A, B and C respectively. Median age (range)=62 (43-74). Male/female=31/23, ECOG PS 0/1=14/40. Median # of vaccines was 3 (range 0-6) and total # vaccines administered was 114. AEs associated with vaccine were mild and no grade 3-4 AE was vaccine related. OR to vaccine was observed in 3/36 patients. OR to paclitaxel (or other second line treatment) was seen in 1/11, 2/12 and 3/14 patients for arms A, B and C respectively. Only arm C moved to stage two. An additional 15 patients have been accrued to the Arm C second stage of the trial and their study data and results is currently being collected for the proposed protocol analysis (Alberto A, et al. J Thoracic Oncol (LA-LCA Supplement) 2014).

Figure 5:
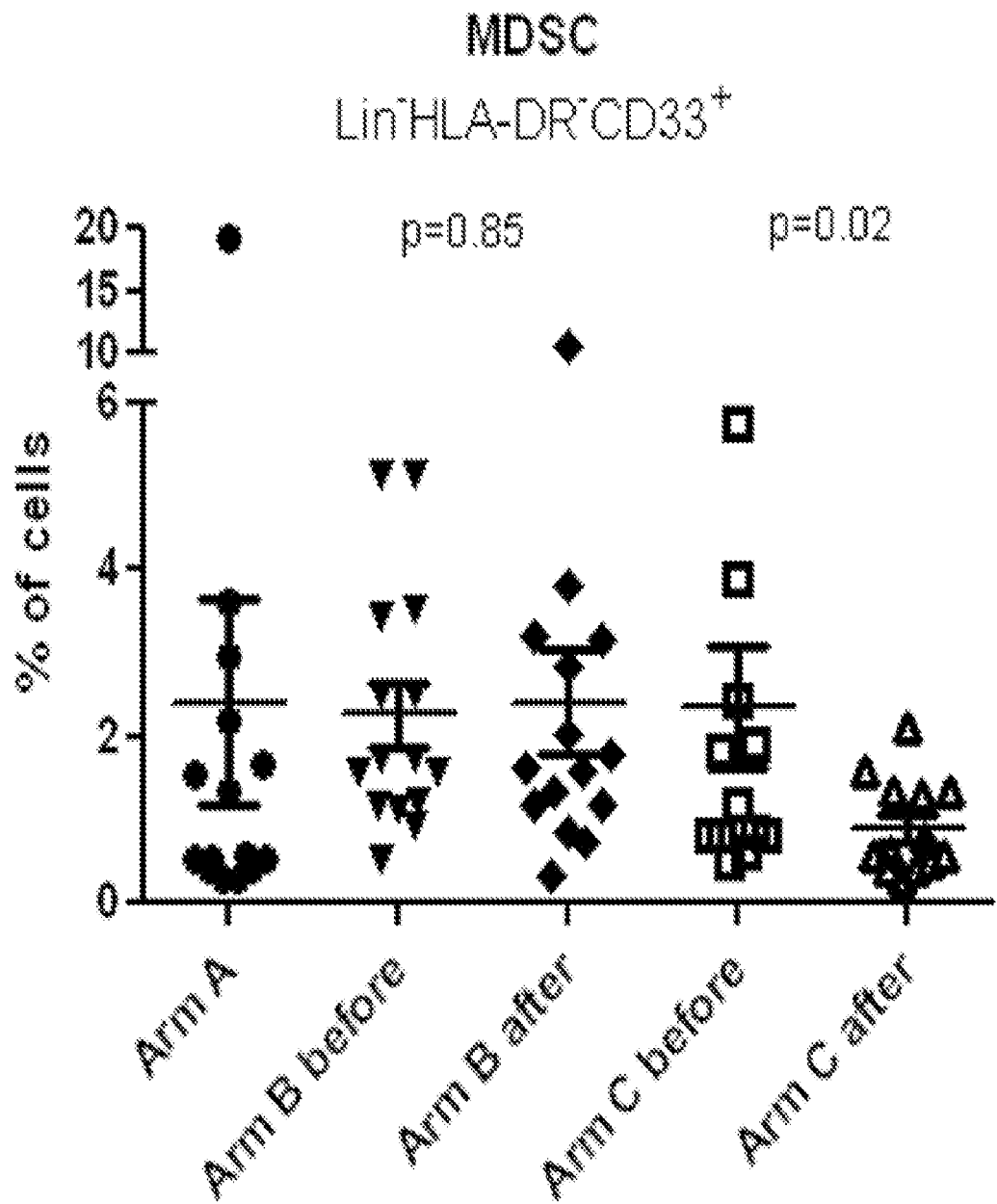
FIG. 5 is a plot showing proportion of MDSCs from patients enrolled in arms A, B, and C (see Table 2), taken before and after immunization.

Pre-treatment levels of MDSC populations in patients from all three arms was similar (p>0.07). Treatment of patients from arm B with vaccine alone did not affect the proportion of MDSC (FIG. 5), whereas in patients treated with ATRA the presence of Lin⁻HLA-DR⁻CD33⁺ MDSC decreased more than two-fold (p=0.02). The proportion of CD11b⁺CD14⁻CD33⁺ MDSC decreased less dramatically but also significantly (p=0.03). No significant differences were observed in the proportion of conventional DC and Treg (Iclozan C, et al. Cancer Immunol Immunother 2013 62:909-18).

Figure 6:
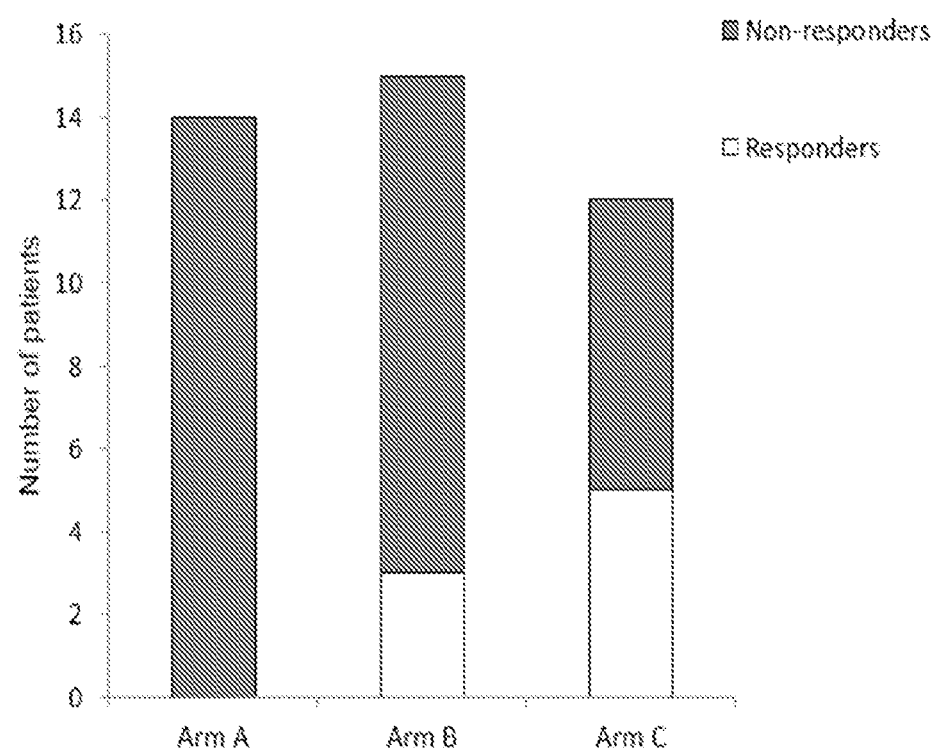
FIG. 6 is a bar graph showing number or patients in arms A, B, and C that were responders.

Next, the p53-specific immune response was evaluated using IFN-γ ELISPOT assay. Prior to start of the treatment no patients had detectable p53 specific response. Consecutive measurements did not show positive p53 responses in any of the arm A patients. After three immunizations, 3 out of 15 tested patients (20%) from arm B met the criteria for p53-specific immune response, which was not significantly different from arm A (p=0.22). In contrast, in arm C 5 out of 12 patients (41.7%) had detectable p53 response, which was significantly higher than in control group (p=0.012) (FIG. 6) (Iclozan C, et al. Cancer Immunol Immunother 2013 62:909-18).

The proportion of p53-specific IFN-γ positive cells CD4⁻ and CD8⁺ T cells was evaluated using intracellular cytokine staining. Prior to the treatment no statistically significant differences between the arms were seen (p>0.07). The immunization significantly increased the proportion IFN-γ positive CD8⁺ and CD4⁺ T cells. The proportion of granzyme B (GrzB) positive CD8⁺ T cells was increased only in patients from arm C but not from arm B (Iclozan C, et al. Cancer Immunol Immunother 2013 62:909-18).

To evaluate the possible link between the immune response to vaccination and the clinical outcome, patients in arms B and C were split based on the presence of p53 specific responses after vaccination. Patients who did not develop immune response had median survival of 11.7 months, as compared with 16.4 months in patients who developed p53 immune responses (hazard ratio 0.52, 95% CI 0.22-1.22) (p=0.1). Patients with brief immune response had the same median survival as non-responders (11.1 months vs. 11.7 months). In contrast, patients who had p53 immune response at least two months after completion of the vaccination had median survival of 41 months (hazard ratio 0.26 (0.09-0.74), p=0.03) suggesting that improving upon the immune response obtained through this strategy could manifest in clinical outcome improvement for patients (Iclozan C, et al. Cancer Immunol Immunother 2013 62:909-18).

Example 4

The programmed cell death 1 (PD-1) pathway represents a major immune control switch which may be engaged by tumor cells to overcome active T-cell immune surveillance. MK-3475 (previously known as SCH 900475) is a potent and highly selective humanized monoclonal antibody (mAb) of the IgG4/kappa isotype designed to directly block the interaction between PD-1 and its ligands, PD-L1 and PD-L2. This blockade enhances functional activity of the target lymphocytes to facilitate tumor regression and ultimately immune rejection.

MK-3475 is a potent humanized IgG4 mAb with high specificity of binding to the PD-1 receptor, thus inhibiting its interaction with PD-L1 and PD-L2. Based on preclinical in vitro data, MK-3475 has high affinity and potent receptor blocking activity for PD-1. MK-3475 has an acceptable preclinical safety profile and is being advanced for clinical development as an IV immunotherapy for advanced malignancies.

Many studies have evaluated the PD-1/PD-L1 inhibitors in the treatment of advanced stage NSCLC. In summary, overall response rates were ~18% with indications that (1) responses were durable and (2) PD-L1 positivity played a role in response (Brahmer J R, et al. N Engl J Med. 2012 366:2455-65; Topalian S L, et al. N Engl J Med. 2012 366:2443-54). Immune-related toxicities were seen with both compounds, including pneumonitis at a rate of 3% with the PD-1 inhibitor (Brahmer J R, et al. N Engl J Med. 2012 366:2455-65). Most of these adverse events improved with drug cessation and treatment with glucorticocorticoids/endocrine therapy replacement where appropriate.

A phase I study of MK-3475 (PD-1 inhibitor) in patients with advanced stage NSCLC refractory to 2 lines of prior treatment was conducted. Thirty-eight patients were enrolled. The overall objective response rate was 24% using investigator-assessed immune-related response criteria (irRC). Six of 9 (67%, 95% CI 30-93%) patients with PD-L1 high tumors responded to therapy versus 0/22 (0%, 95% CI 0-15%) patients with PD-L1 low tumors. The most common drug-related adverse events were rash, pruritus, and fatigue (16% each), and diarrhea (13%). The only grade 3/4 event was one patient who developed grade 3 pulmonary edema. There were no drug-related deaths.

A phase I study was also conducted that randomized 217 patients with known PD-L1 status to MK-3475 10 mg/kg every 2 weeks (Q2W) and MK-3475 10 mg/kg every 3 weeks (Q3W) (Garon E B. J Clin Oncol 32:5s, 2014 (suppl; abstr 8020)). The overall response rate (ORR) in all patients was 18% (95% CI 13-24%) by irRC and 20% (95% CI 15-26%) by RECIST v1.1. Patients with PD-L1 expressing tumors had ORR of 19% (95% CI 14-26%) by irRC and 23% (16-30%) by RECIST. Patients with PD-L1 negative tumors had ORR of 13% (95% CI 4-27%) by irRC and 9% (2-23%) by RECIST. At the interim analysis, there was no statistical difference in response rates in the different dosage groups. The most common drug-related adverse events included fatigue (13%), decreased appetite (6.5%), arthralgia (6.1%), pruritus (5.4%), and pyrexia (3.6%) and most of these were grade 1/2. Six percent of patients had grade 3/4 drug-related adverse events. Four patients (2 patients in each schedule) developed grade 3/4 pneumonitis.

The efforts in cancer immune therapy are focused on increasing the frequency of CTL-mediated tumor destruction by applying cancer vaccines, adoptively transferred antigen-specific T cells, inhibitors of check-point blockade (CTLA4, PD-1) or other immune therapeutics (Mellman I, et al. Nature 2011 480:480-9). However, even in tumor-bearing mice, once tumors are established these interventions have relatively limited efficacy, and the rate of clinical responses in cancer patients, although encouraging, remains relatively low (Restifo N P, et al. Nat Rev Immunol 2012 12:269-81; Pardoll D, et al. J Exp Med 2012 209:201-9).

Ad.p53-DC has demonstrated to be safe and to produce specific cytotoxic immune responses in patients with SCLC. Depletion of MDSC with ATRA, substantially improved the immune response to Ad.p53-DC vaccination suggesting that this approach can be used to enhance the effect of immune interventions in cancer.

The programmed cell death 1 (PD-1) pathway represents a major immune control switch which may be engaged by tumor cells to overcome active T-cell immune surveillance. MK-3475 is a potent humanized IgG4 mAb with high specificity of binding to the PD-1 receptor, thus inhibiting its interaction with PD-L1 and PD-L2. This blockade enhances functional activity of the target lymphocytes to facilitate tumor regression and ultimately immune rejection.

Thus, these 3 individually safe, partially effective, and apparently synergistic strategies can be combined into one single strategy.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A method for treating a human subject having cancer, comprising administering to the human subject a therapeutically effective amount of dendritic cells engineered to express adenoviral p53 (Adp53/DC), and a therapeutically effective amount of an immune checkpoint inhibitor (ICI), wherein the ICI is anti-PD-1 antibody, anti-PD-L1 antibody or anti-PD-L2 antibody.

2. The method of claim 1, wherein the Adp53/DC and ICI are co-administered.

3. The method of claim 1, wherein the Adp53/DC and ICI are administered sequentially.

4. The method of claim 1, wherein the Adp53/DC cells comprise a nucleic acid encoding p53 operably linked to an expression control sequence.

5. The method of claim 1, wherein the cancer is a sarcoma, lymphoma, leukemia, carcinoma, blastoma, or germ cell tumor.

6. The method of claim 5, wherein the cancer is a lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, small cell lung cancer, non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, epithelial cancer, renal cancer.

7. The method of claim 6, wherein the cancer is small cell lung cancer.

8. The method of claim 1, further comprising administering to the human subject an additional anti-cancer treatment.

9. The method of claim 8, wherein the additional anti-cancer treatment includes passive or active immunotherapy.

10. The method of claim 1, wherein a least 2 doses of Adp53/DC are administered to the human subject.

11. The method of claim 10, wherein each dose of Adp53/DC contains from $1\times10^6$ to $1\times10^7$ DCp53 cells.

12. The method of claim 1, wherein the Adp53/DC is administered at 1, 2, 3, 4, 5, 6-day intervals or 1, 2, 3, or 4 week intervals.

13. The method of claim 10, wherein the Adp53/DC are administered in three doses.

14. The method of claim 11, wherein the dendritic cell doses are administered at two-week intervals.

15. The method of claim 1, further comprising administering to the human subject a therapeutically effective amount of all-trans-retinoic acid (ATRA).

16. The method of claim 15, wherein the ATRA is administered to the human subject at least three days prior to administration of the dendritic cells.

17. The method of claim 1, wherein the human subject has been treated with an anti-cancer therapy prior to the administration of the Adp53/DC and ICI.

18. The method of claim 1, wherein the dendritic cells are autologous.

19. The method of claim 1, wherein the Adp53/DC is administered intra-dermally.

20. The method of claim 1, wherein the ICI is anti-PD-1 antibody.

21. The method of claim 1, wherein the ICI is anti-PD-L1 antibody.

22. The method of claim 1, wherein the ICI is anti-PD-L2 antibody.

* * * * *